United States Patent
Iizuka et al.

(10) Patent No.: US 9,341,599 B2
(45) Date of Patent: May 17, 2016

(54) ULTRASONIC FLAW DETECTION METHOD, ULTRASONIC FLAW DETECTION APPARATUS, AND PIPE MANUFACTURING METHOD

(75) Inventors: Yukinori Iizuka, Tokyo (JP); Takafumi Ozeki, Tokyo (JP); Yutaka Matsui, Tokyo (JP)

(73) Assignee: JFE Steel Corporation (JP)

(*) Notice: Subject to any disclaimer, the term of this patent is extended or adjusted under 35 U.S.C. 154(b) by 0 days.

(21) Appl. No.: 14/374,989

(22) PCT Filed: May 9, 2012

(86) PCT No.: PCT/JP2012/061836
§ 371 (c)(1),
(2), (4) Date: Jul. 28, 2014

(87) PCT Pub. No.: WO2013/114639
PCT Pub. Date: Aug. 8, 2013

(65) Prior Publication Data
US 2015/0000095 A1  Jan. 1, 2015

(30) Foreign Application Priority Data
Jan. 31, 2012 (JP) .................. 2012-017895

(51) Int. Cl.
*G01N 29/07* (2006.01)
*G01N 29/04* (2006.01)
(Continued)

(52) U.S. Cl.
CPC ............ *G01N 29/043* (2013.01); *G01N 29/041* (2013.01); *G01N 29/07* (2013.01);
(Continued)

(58) Field of Classification Search
CPC . G01N 29/043; G01N 29/11; G01N 29/4454; G01N 29/041; G01N 29/265; G01N 2291/0289; G01N 2291/0234; G01N 2291/2634; Y10T 29/49764
USPC ............................................ 73/602, 622, 623
See application file for complete search history.

(56) References Cited

U.S. PATENT DOCUMENTS 5,150,714 A * 9/1992 Green ........................ 600/442
5,557,970 A * 9/1996 Abbate et al. .................. 73/597

FOREIGN PATENT DOCUMENTS

| JP | 04-009659 A | 1/1992 |
| JP | 06-317418 A | 11/1994 |

(Continued)

OTHER PUBLICATIONS

Extended European Search Report dated Jul. 9, 2015 from corresponding European Patent Application No. 12 86 7508.
(Continued)

*Primary Examiner* — Laura Martin
*Assistant Examiner* — Rose M Miller
(74) *Attorney, Agent, or Firm* — DLA Piper LLP (US)

(57) ABSTRACT

An ultrasonic flaw detection method to detect flaws on an inner surface of a metallic pipe using ultrasonic waves includes a waveform hold step that acquires and holds waveform data of an echo signal when an ultrasonic probe that generates ultrasonic signals toward the inner surface and the metallic pipe are moved relative to each other, a signal analyzing step that calculates a path length up to receiving an echo signal from the inner surface and a change rate of the path length based on the waveform data held, and a flaw detecting step that detects flaws on the inner surface based on the path length and the change rate of the path length.

6 Claims, 12 Drawing Sheets

(51) Int. Cl.
  *G01N 29/265* (2006.01)
  *G01N 29/11* (2006.01)
  *G01N 29/44* (2006.01)

(52) U.S. Cl.
  CPC ............ *G01N 29/11* (2013.01); *G01N 29/265* (2013.01); *G01N 29/4427* (2013.01); *G01N 2291/0234* (2013.01); *G01N 2291/0289* (2013.01); *G01N 2291/2634* (2013.01); *Y10T 29/49764* (2015.01)

(56) References Cited

FOREIGN PATENT DOCUMENTS

| JP | 2002-031625 A | 1/2002 |
|---|---|---|
| JP | 2003-121425 A | 4/2003 |
| JP | 2003-302381 A | 10/2003 |
| JP | 2006-132981 A | 5/2006 |
| JP | 2008-070325 A | 3/2008 |
| JP | 2010-25807 | 2/2010 |
| JP | 2011-153974 A | 8/2011 |

OTHER PUBLICATIONS

Notice of Grounds for Rejection dated Dec. 3, 2015 of corresponding Korean Patent Application No. 10-2014-7021328 along with an English translation.

Notice of Rejection dated Aug. 18, 2015 of corresponding Japanese Patent Application No. 2012-017895 along with an English translation.

Notification of First Office Action dated Sep. 2, 2015 from corresponding Chinese Patent Application No. 201280068720.0 along with an English translation.

\* cited by examiner

ULTRASONIC FLAW DETECTION METHOD, ULTRASONIC FLAW DETECTION APPARATUS, AND PIPE MANUFACTURING METHOD

TECHNICAL FIELD

This disclosure relates to ultrasonic flaw detection methods, ultrasonic flaw detection apparatuses, and pipe manufacturing methods that detect flaws on the inner surface of a test subject such as a metallic pipe using ultrasonic waves.

BACKGROUND

As a quality assurance measure to detect flaws arising during the manufacture of metallic steel products such as steel pipes, steel bars, steel shapes, and planks, ultrasonic flaw detection methods that use ultrasonic waves have been widely applied. For example, for metallic pipes such as steel pipes, angle beam flaw detection and normal beam flaw detection are usually used. The angle beam flaw detection is applied to detect crack-like flaws arising mainly on the inner and outer surfaces of a metallic pipe, and angle probes are so arranged that the beam directions of ultrasonic waves are in two directions each in the axial direction of the pipe and in the circumferential direction thereof, more specifically, in a total of four directions, such that flaws that are parallel in the axial direction of the pipe or in the circumferential direction thereof are easily detected. Meanwhile, normal beam flaw detection is applied to detect inclusions included inside the metallic pipe and to measure wall thickness. Using such an ultrasonic flaw detection method, inspection of a test subject is conducted spirally on the entire surface and in the entire length thereof while the steel pipe or the probes are rotated. In the conventional ultrasonic flaw detection method, flaw detection is performed in which the presence of flaw echo is determined on each occasion of a single transmission and reception of ultrasonic waves.

In the conventional ultrasonic flaw detection method for metallic pipes in the foregoing, however, because the reflecting surface of a dent flaw by jamming of contaminants in rolling or a shallow flaw in a lapped form has an angle with respect to the planes in both cross-sectional direction and length direction, there has been a drawback of a flaw echo signal being weak in both the angle beam flaw detection and the normal beam flaw detection. Furthermore, such a dent flaw and a shallow flaw in a lapped form are shallow in depth. Thus, the separation of bottom echo is not easy in the normal beam flaw detection. As a consequence, by angle beam flaw detection and normal beam flaw detection, it has been difficult to detect a dent flaw by jamming of contaminants in rolling and a shallow flaw in a lapped form. For the outer surface of the metallic pipes, it is possible to detect the above-described flaws by the combination use of leak-age-flux flaw detection and eddy-current flaw detection. However, there are no appropriate detection measures for the inner surface of the metallic pipes. Thus, a visual inspection is needed.

Japanese Laid-open Patent Publication No. 2008-70325 describes detection of a flaw in the vicinity of the surface of a metallic pipe by an ultrasonic flaw detection method. In JP '325, a two-dimensional image is generated in which flaw detection signals acquired while moving are combined by adjusting the positions of the signals such that bottom echoes are aligned, and a flaw is then extracted from the two-dimensional image.

Meanwhile, depending on the shape of a flaw, there may be no flaw echo present and the bottom echo itself may fluctuate. In such a case, the ultrasonic flaw detection method described in JP '325 acquires a two-dimensional image in which beam path lengths are aligned at the detected position of the bottom echo to detect a subsurface flaw in the vicinity of the surface. With the two-dimensional image, however, because the detected position of the bottom echo is referenced, it cannot detect a flaw that is on the inner surface of the metallic pipe. Furthermore, when the incident ultrasonic waves scatter at the bottom and the bottom echo itself is weak, detection of bottom echo itself is difficult even when the method described in JP '325 is attempted to be applied. Thus, it is not feasible to align the beam path lengths at the detected position of the bottom echoes. Consequently, detection of flaws on the inner surface of the metallic pipes such as steel pipes has to depend upon a visual inspection.

In view of the foregoing, there is a need to provide an ultrasonic flaw detection method, an ultrasonic flaw detection apparatus, and a pipe manufacturing method capable of detecting even a dent flaw or a shallow flaw in a lapped form arisen on the inner surface of a metallic pipe such as a steel pipe.

SUMMARY

We thus provide:

Ultrasonic flaw detection methods of detecting a flaw on an inner surface of a metallic pipe using ultrasonic waves including: waveform holding step for acquiring and holding waveform data of an echo signal when an ultrasonic probe that generates ultrasonic signals toward the inner surface and the metallic pipe are moved relative to each other; signal analyzing step for calculating a path length up to receiving an echo signal from the inner surface and a change rate of the path length based on the waveform data held; and flaw detecting step for detecting a flaw on the inner surface based on the path length and the change rate of the path length.

The flaw detecting step can determine that a flaw is present in a portion satisfying a condition in which the path length is equal to or smaller than a given path length threshold or the change rate of the path length is equal to or greater than a given path-length change rate threshold, and that no flaw is present in a portion not satisfying the condition.

The signal analyzing step can further calculate a height of the echo signal from the inner surface based on the waveform data held, and the flaw detecting step determines that a flaw is present in a portion satisfying a condition in which the path length is equal to or smaller than a given path length threshold, or the change rate of the path length is equal to or greater than a given path-length change rate threshold and the height is equal to or smaller than a given height threshold, and that no flaw is present in a portion not satisfying the condition.

The signal analyzing step can further calculate a height of the echo signal from the inner surface based on the waveform data held, and the flaw detecting step determines that a flaw is present in a portion satisfying a condition in which the path length is equal to or smaller than a given path length threshold, or the change rate of the path length is equal to or greater than a given path-length change rate threshold and the height within a search range preset with respect to a position of the change rate of the path length being equal to or greater than a given path-length change rate threshold as a reference position is equal to or smaller than a given height threshold, and that no flaw is present in a portion not satisfying the condition.

The signal analyzing step can analyze a noise level of noise components in a portion in which no echo signal is present based on the waveform data held, determines a threshold to detect an echo signal based on the analysis result, and detects the echo signal based on the determined threshold to calculate the path length.

An ultrasonic flaw detection apparatus detects a flaw on an inner surface of a metallic pipe using ultrasonic waves and includes a waveform holding unit that acquires and holds waveform data of an echo signal when an ultrasonic probe that generates ultrasonic signals toward the inner surface and the metallic pipe are moved relative to each other; a signal analyzing unit that calculates a path length up to receiving an echo signal from the inner surface and a change rate of the path length based on the waveform data held; and a flaw detecting unit that detects a flaw on the inner surface based on the path length and the change rate of the path length.

The flaw detecting unit can determine that a flaw is present in a portion satisfying a condition in which the path length is equal to or smaller than a given path length threshold or the change rate of the path length is equal to or greater than a given path-length change rate threshold, and determines that no flaw is present in a portion not satisfying the condition.

The signal analyzing unit can further calculate a height of the echo signal from the inner surface based on the waveform data held, and the flaw detecting unit determines that a flaw is present in a portion satisfying a condition in which the path length is equal to or smaller than a given path length threshold, or the change rate of the path length is equal to or greater than a given path-length change rate threshold and the height is equal to or smaller than a given height threshold, and determines that no flaw is present in a portion not satisfying the condition.

The signal analyzing unit can further calculate a height of the echo signal from the inner surface based on the waveform data held, and the flaw detecting unit determines that a flaw is present in a portion satisfying a condition in which the path length is equal to or smaller than a given path length threshold, or the change rate of the path length is equal to or greater than a given path-length change rate threshold and the height within a search range preset with respect to a position of the change rate of the path length being equal to or greater than a given path-length change rate threshold as a reference position is equal to or smaller than a given height threshold, and determines that no flaw is present in a portion not satisfying the condition.

The signal analyzing unit can analyze a noise level of noise components in a portion in which no echo signal is present based on the waveform data held, determines a threshold to detect an echo signal based on the analysis result, and detects the echo signal based on the determined threshold to calculate the path length.

A pipe manufacturing method for manufacturing a pipe includes performing at least a heating process, a piercing process, a rolling process, a reheating process, a shaping process, and an inspection process on a metallic material, and the inspection process includes: waveform holding step for acquiring and holding waveform data of an echo signal when an ultrasonic probe that generates ultrasonic signals toward an inner surface of the pipe and the pipe are moved relative to each other; signal analyzing step for calculating a path length up to receiving an echo signal from the inner surface and a change rate of the path length based on the waveform data held; and flaw detecting step for detecting a flaw on the inner surface based on the path length and the change rate of the path length.

The flaw detecting step can determine that a flaw is present in a portion satisfying a condition in which the path length is equal to or smaller than a given path length threshold or the change rate of the path length is equal to or greater than a given path-length change rate threshold, and that no flaw is present in a portion not satisfying the condition.

The signal analyzing step can further calculate a height of the echo signal from the inner surface based on the waveform data held, and the flaw detecting step determines that a flaw is present in a portion satisfying a condition in which the path length is equal to or smaller than a given path length threshold, or the change rate of the path length is equal to or greater than a given path-length change rate threshold and the height is equal to or smaller than a given height threshold, and that no flaw is present in a portion not satisfying the condition.

The signal analyzing step can further calculate a height of the echo signal from the inner surface based on the waveform data held, and the flaw detecting step determines that a flaw is present in a portion satisfying a condition in which the path length is equal to or smaller than a given path length threshold, or the change rate of the path length is equal to or greater than a given path-length change rate threshold and the height within a search range preset with respect to a position of the change rate of the path length being equal to or greater than a given path-length change rate threshold as a reference position is equal to or smaller than a given height threshold, and that no flaw is present in a portion not satisfying the condition.

The signal analyzing step can analyze a noise level of noise components in a portion in which no echo signal is present based on the waveform data held, determines a threshold to detect an echo signal based on the analysis result, and detects the echo signal based on the determined threshold to calculate the path length.

A path length up to receiving an echo signal from an inner surface of the steel product and a change rate of the path length are calculated based on waveform data of the echo signal acquired while a metallic pipe and an ultrasonic probe are moved relative to each other, and based on the path length and the change rate of the path length, a flaw on the inner surface is detected. Consequently, even a dent flaw or a shallow flaw in a lapped form arising on the inner surface of the metallic pipe such as a steel pipe can be detected.

REFERENCE SIGNS LIST

Figure 1:
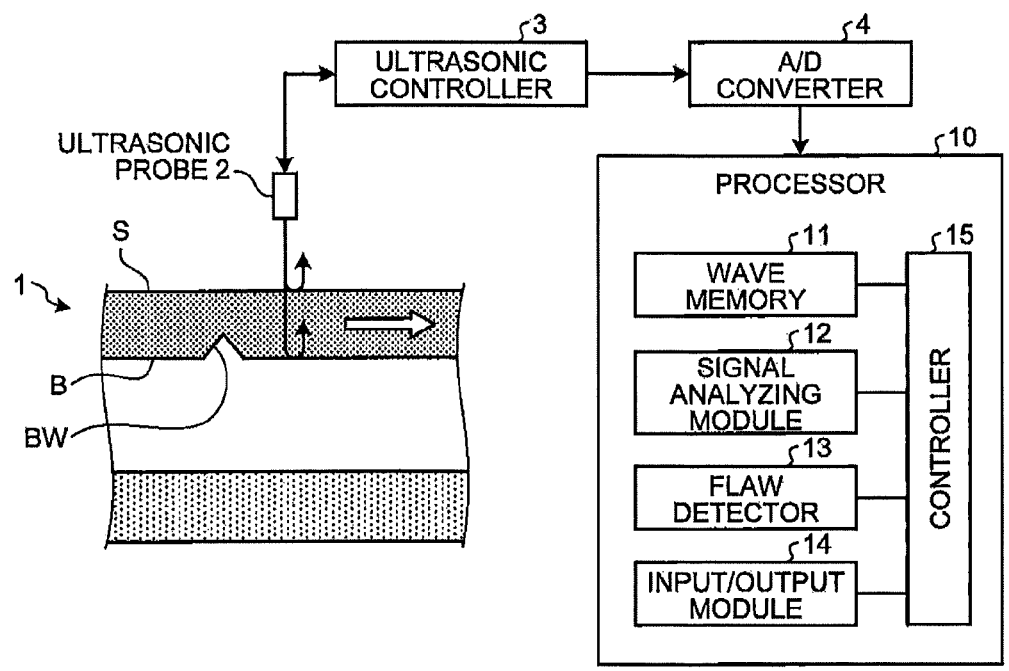
FIG. 1 is a schematic diagram illustrating the configuration of an ultrasonic flaw detection apparatus according to a first example.

1 steel pipe
2 ultrasonic probe
3 ultrasonic controller
4 A/D converter
10 processor
11 wave memory
12 signal analyzing unit
13 flaw detector
14 input/output unit
15 controller
ES surface echo
EB bottom echo
S outer surface
B inner surface
BW, 31, 32 flaw
DA, DB, DC, DC2, L1, L2 threshold
LN noise level

DETAILED DESCRIPTION

With reference to the accompanying drawings, the following describes an ultrasonic flaw detection method, an ultrasonic flaw detection apparatus, and a pipe manufacturing method that are examples of our methods and apparatus.

First Configuration

FIG. 1 is a schematic diagram illustrating the configuration of an ultrasonic flaw detection apparatus according to a first example. As illustrated in FIG. 1, the first example is a situation to detect a flaw BW that is present on an inner surface B of a steel pipe 1 as a metallic pipe that is a test subject. The flaw BW includes a dent flaw by jamming of contaminants in rolling and a shallow flaw in a lapped form. Near an outer surface S of the steel pipe 1, provided is an ultrasonic probe 2 that transmits and receives ultrasonic signals. The steel pipe 1 and the ultrasonic probe 2 move relative to each other about the steel pipe 1 in a spiral manner. In the relative movement, the steel pipe 1 may be rotated and moved while the ultrasonic probe 2 is fixed, the ultrasonic probe 2 may be revolved and moved around the steel pipe 1 while the steel pipe 1 is fixed, or both the steel pipe 1 and the ultrasonic probe 2 may be moved.

An ultrasonic controller 3 controls transmitting and receiving of ultrasonic signals by the ultrasonic probe 2, and outputs the ultrasonic signals received at a given pitch to an A/D converter 4. The A/D converter 4 converts the ultrasonic signals received that are analog signals into a digital signal and outputs it to a processor 10. The analog ultrasonic signal here is an RF signal received as it is or is a signal detected by the ultrasonic controller 3, and is A-scope data that is drawn with time (distance) information as the abscissa axis and signal amplitude information as the ordinate axis. The A/D converter 4 has a sampling frequency and resolution sufficient to sample the A-scope data.

The processor 10 includes a wave memory 11, a signal analyzing unit 12, a flaw detector 13, an input/output unit 14, and a controller 15. The wave memory 11, under the control of the controller 15, holds the A-scope data of the steel pipe 1 for a designated section including the entire length thereof or a specific zone thereof as B-scope data (see FIG. 3). The B-scope data is drawn with the direction (a moving distance) as the abscissa axis and the distance of ultrasonic signal in the transmitting and receiving direction as the ordinate axis, and is drawn as a tomogram. Consequently, the wave memory has a capacity that can hold the B-scope data for the entire length of or a designated section of the steel pipe 1. For example, when flaw detection is performed on a steel pipe of 20 millimeters thick and 10 meters long with an ultrasound of 5 megahertz at a pitch of 1 millimeter, a sampling frequency is 25 megahertz (sampling period=0.04 μsec), an A/D conversion time needs to be 10 μsec as one and half times the thickness, one waveform is measured at 250 points (10 μsec/0.04 μsec=250), and 10,000 pulse waveforms result for the entire length (when inspected not in a spiral manner but linearly in the long direction). In this case, the wave memory 11 needs to have a memory capacity that can store therein two-dimensional data of 250×10,000 points.

Figure 2:
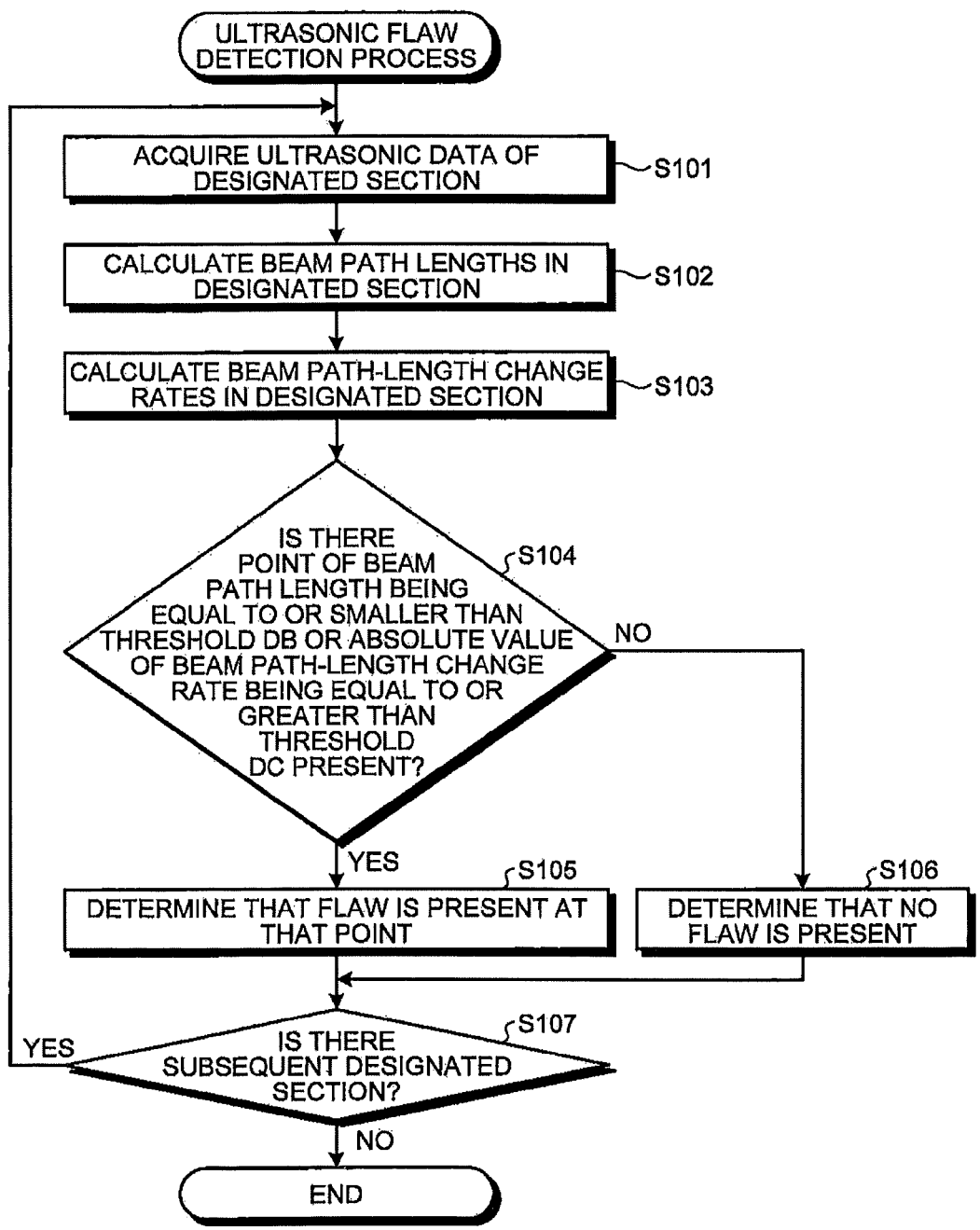
FIG. 2 is a flowchart illustrating a procedure for an ultrasonic flaw detection process performed by a processor in the first example.

With reference to the flowchart illustrated in FIG. 2, the following describes a procedure for an ultrasonic flaw detection process performed by the processor 10 in the first example. The controller 15 first acquires ultrasonic data (B-scope data) of a designated section received from the A/D converter 4, and stores them in the wave memory 11 in sequence (Step S101).

The signal analyzing unit 12 calculates a beam path length of each of the pulse waveforms from the ultrasonic data stored in the wave memory 11 (Step S102). The beam path length is a distance obtainable from the time from when a surface echo ES reflected from the outer surface S of the steel pipe 1 is received until a bottom echo EB reflected from the inner surface B of the steel pipe 1 is received (see FIGS. 1 and 3). When the distance between the ultrasonic probe 2 and the outer surface S of the steel pipe 1 is held, the surface echo ES may be replaced with the occurrence location (occurrence time) of a transmitted pulse, and the path length may be obtained as the time from this occurrence time until the bottom echo EB is received. The path length of each pulse obtained is as illustrated in FIG. 4(*d*). The detecting position of the bottom echo EB may be a peak position of the bottom echo or a position thereof to cross a given threshold.

The signal analyzing unit 12 then calculates an amount of change in the beam path length with respect to a relative moving amount between the steel pipe 1 and the ultrasonic probe 2, more specifically, a beam path-length change rate (Step S103). For example, the beam path-length change rate can be obtained from the following Expression 1:

$$\text{Beam path-length change rate} = (\text{Beam path length} - \text{Beam path length of one pulse previous})/\text{Moving amount of one pulse} \quad (1)$$

The beam path-length change rates obtained are as illustrated in FIG. 4(*e*).

Subsequently, as illustrated in FIG. 4, the flaw detector 13 determines whether there is a point present at which the beam path length is equal to or smaller than a threshold DB (see FIG. 4(*d*)), or the absolute value of the beam path-length change rate is equal to or greater than a threshold DC (see FIG. 4(*e*)) (Step S104). If the point at which the beam path length is equal to or smaller than the threshold DB, or the absolute value of the beam path-length change rate is equal to or greater than the threshold DC is present (Yes at Step S104), the flaw detector 13 determines that a flaw is present at the point (location) at which this condition is satisfied (Step S105). Meanwhile, if the point at which the beam path length is equal to or smaller than the threshold DB, or the absolute value of the beam path-length change rate is equal to or greater than the threshold DC is not present (No at Step S104), the flaw detector 13 determines that no flaw is present in the designated section (Step S106).

The flaw detector 13 then determines whether there is a subsequent designated section present (Step S107). If a subsequent designated section is present (Yes at Step S107), the flaw detector 13 moves back to the process at Step S101 to perform the above-described process on the subsequent designated section, and if a subsequent designated section is not present (No at Step S107), the flaw detector 13 ends the present process. The input/output unit 14 is a unit that outputs the detection result of the flaw detector 13, and is a unit on which various operation input necessary for the processor 10 is performed.

Determining whether the beam path length is equal to or smaller than the threshold DB is suitable for detecting poor wall thickness of the steel pipe 1, and determining whether the absolute value of the beam path-length change rate is equal to or greater than the threshold DC is suitable for detecting a point at which a steep fluctuation in wall thickness is located. The use of such beam path length and beam path-length change rate can accurately detect dents by jamming of contaminants in rolling and shallow flaws in a lapped form.

Figure 3:
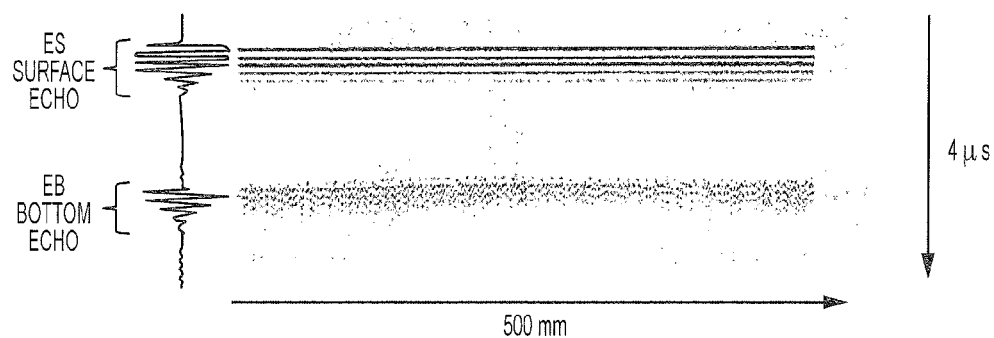
FIG. 3 is a diagram illustrating an example of ultrasonic data stored in a wave memory.
Figure 4:
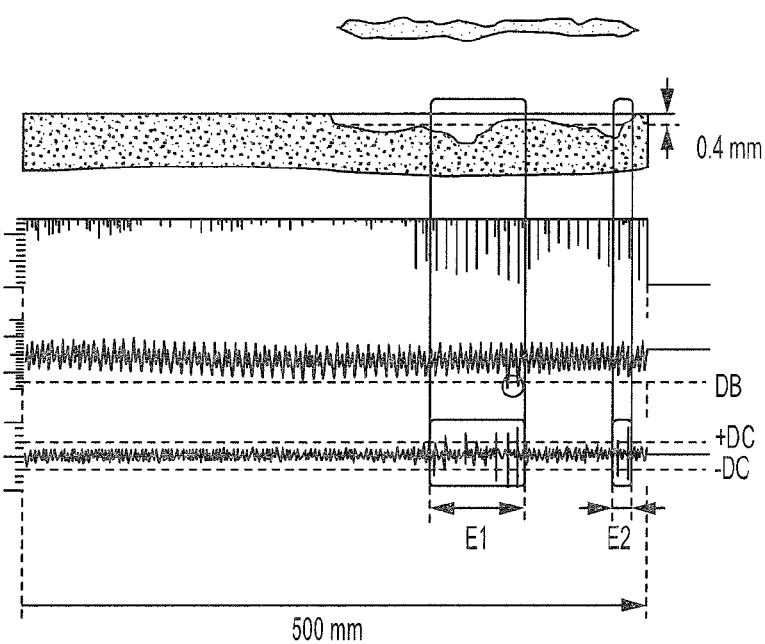
FIG. 4 includes diagrams illustrating beam path length, beam path-length change rate, and flaw detection result obtained based on the ultrasonic data illustrated in FIG. 3.

FIG. 4 illustrates the result of the beam path lengths and the beam path-length change rates obtained from the ultrasonic data illustrated in FIG. 3 stored in the wave memory 11. FIG. 4 illustrates the result obtained with a measurement length of 500 millimeters as the designated section, and flaws are determined to be present in areas E1 and E2. In fact, in the areas E1 and E2, as illustrated in FIG. 4(*b*), there are flaws present with a depth of 0.4 millimeters or more. FIG. 4(*a*) illustrates a plan view of a flaw, and FIG. 4(*b*) illustrates a cross-sectional view of the steel pipe 1. FIG. 4(*c*) illustrates echo height that is a maximum amplitude of the bottom echo EB for reference.

Second Configuration

Figure 5:
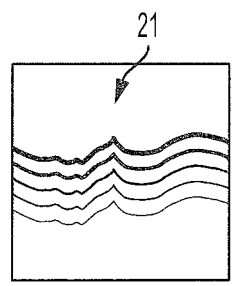
FIG. 5 is a diagram illustrating an example of a B-scope near a bottom echo in a flaw portion.

The beam path-length change rate is a type of differential processing, and thus may output a large value due to the influence of noise. Meanwhile, at a flaw portion, because a flaw surface is inclined with respect to the bottom surface, the echo height that is a maximum amplitude of the bottom echo EB drops down drastically. For example, as illustrated in FIG. 5, the bottom echo EB disappears in a portion in which a flaw is present, and a faint echo 21 appears before the bottom echo EB (in the direction of shorter path length (upward direction in FIG. 5)). While it is thus preferable to perform flaw detection by taking the echo height into consideration, the echo height fluctuates due to the condition of a contact medium between the ultrasonic probe 2 and the steel pipe 1, for example. Consequently, it is preferable to take a logical conjunction of the beam path-length change rate and the echo height to complement the weaknesses of the both to improve the accuracy of flaw detection. In a second example, the flaw detection process is performed by taking the echo height into consideration in the process of determining the beam path-length change rate performed in the process in the first example. In this case, the threshold DC for the absolute value of the beam path-length change rate is made stricter (smaller) as a threshold DC2.

Figure 6:
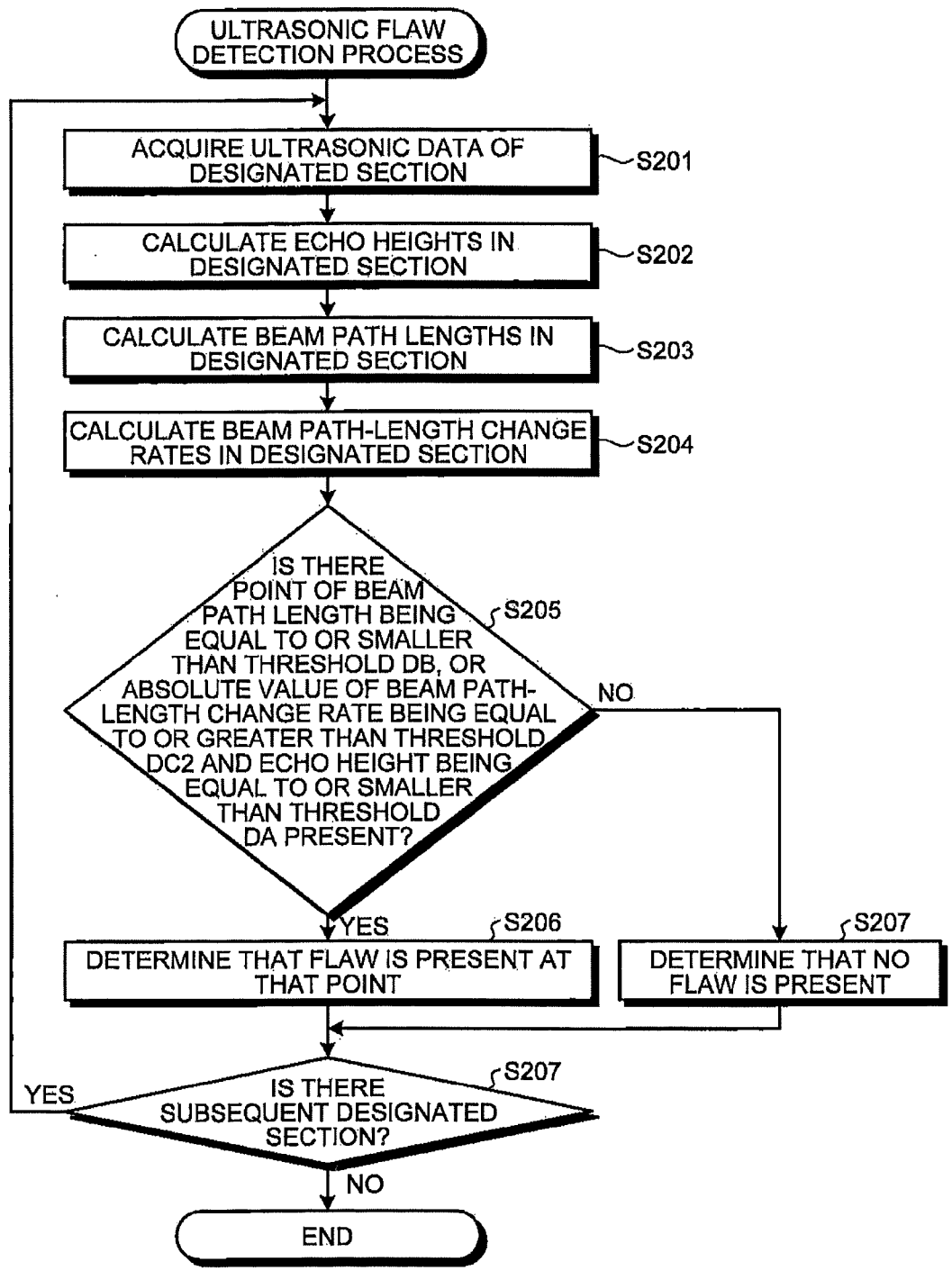
FIG. 6 is a flowchart illustrating a procedure for an ultrasonic flaw detection process performed by a processor according to a second example.

With reference to the flowchart illustrated in FIG. 6, the following describes the procedure for an ultrasonic flaw detection process performed by the processor 10 in the second example. The controller 15, as the same as that in the first example, first acquires ultrasonic data (B-scope data) of a designated section received from the A/D converter 4, and stores them in the wave memory 11 in sequence (Step S201).

The signal analyzing unit 12 then calculates the echo heights of the bottom echoes EB in the designated section from the ultrasonic data stored in the wave memory 11 (Step S202). Furthermore, the signal analyzing unit 12, as the same as that in the first example, calculates the beam path lengths in the designated section at Step S203, and calculates the beam path-length change rates in the designated section at Step S204.

Figure 7:
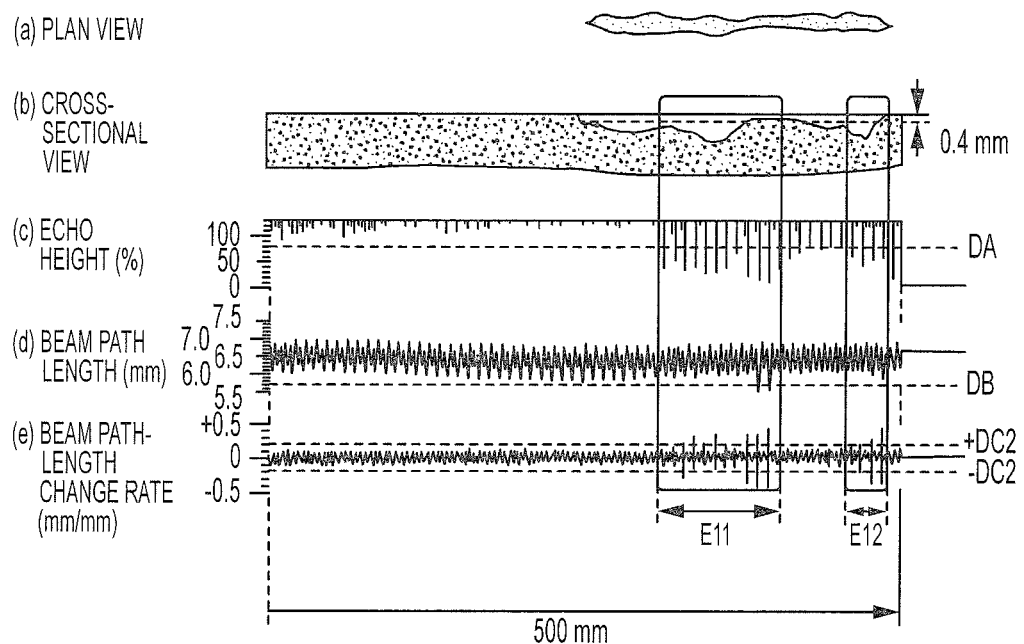
FIG. 7 includes diagrams illustrating echo height, beam path length, beam path-length change rate, and flaw detection result obtained based on the ultrasonic data illustrated in FIG. 3 in the second example.

Then, as illustrated in FIG. 7, the flaw detector 13 determines whether there is a point present at which the beam path length is equal to or smaller than a threshold DB (see FIG. 7(*d*)), or the absolute value of the beam path-length change rate is equal to or greater than a threshold DC2 (see FIG. 7(*e*)) and the echo height is equal to or smaller than a threshold DA (see FIG. 7(*c*)) (Step S205). The threshold DC2 here is a value smaller than that of the threshold DC as described above. When the point at which the beam path length is equal to or smaller than the threshold DB, or the absolute value of the beam path-length change rate is equal to or greater than the threshold DC and the echo height is equal to or smaller than the threshold DA is present (Yes at Step S205), the flaw detector 13 determines that a flaw is present at the point (location) at which this condition is satisfied (Step S206). Meanwhile, when the point at which the beam path length is equal to or smaller than the threshold DB, or the absolute value of the beam path-length change rate is equal to or greater than the threshold DC2 and the echo height is equal to or smaller than the threshold DA is not present (No at Step S205), the flaw detector 13 determines that no flaw is present in the designated section (Step S207). In the B-scope data illustrated in FIG. 7, the flaws are determined to be present at two points of areas E11 and E12.

The flaw detector 13 then determines whether a subsequent designated section is present (Step S208). If a subsequent designated section is present (Yes at Step S208), the flaw detector 13 moves back to the process at Step S201 to perform the above-described process on the subsequent designated section, and if a subsequent designated section is not present (No at Step S208), the flaw detector 13 ends the present process.

In the second example, not only the beam path-length change rate but the logical conjunction of the beam path-length change rate and the echo height is taken, and thus more accurate flaw detection can be performed. Specifically, the areas E11 and E12 illustrated in FIG. 7 are detected in wider ranges than the areas E1 and E2 illustrated in FIG. 4.

Third Configuration

While the detecting position of the bottom echo EB may be either a peak position of the bottom echo or the position thereof to cross a given threshold in the first and the second examples, the given threshold is preferably smaller so that the detecting position of the bottom echo EB can be detected even with a faint bottom echo. Consequently, in the third example, the threshold to detect the bottom echo EB is set to a value that is slightly over a maximum value of noise.

Figure 8:
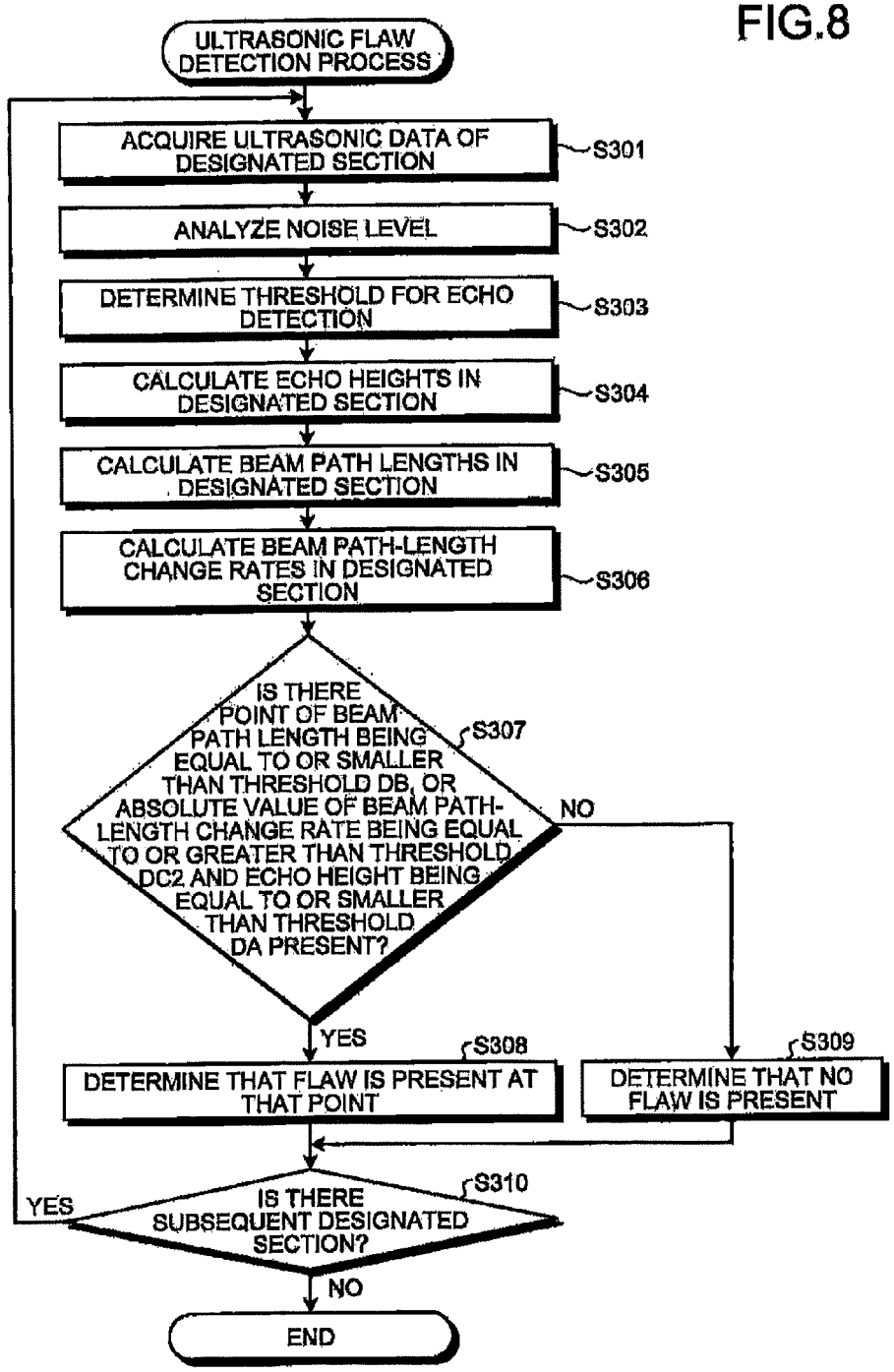
FIG. 8 is a flowchart illustrating a procedure for an ultrasonic flaw detection process performed by a processor according to a third example.

With reference to the flowchart illustrated in FIG. 8, the following describes the procedure for an ultrasonic flaw detection process performed by the processor 10 in the third example. The controller 15, as the same as that in the second example, first acquires ultrasonic data (B-scope data) of a designated section received from the A/D converter 4, and stores them in the wave memory 11 in sequence (Step S301).

Then, the signal analyzing unit 12 analyzes noise level from the ultrasonic data stored in the wave memory 11 (Step S302). Specifically, a maximum value of the noise is obtained. The analysis object of the noise level is an area in which no echo signal is present, and is the ultrasonic data of an area EN illustrated in FIG. 9, for example. Subsequently, the signal analyzing unit 12 determines the threshold to detect bottom echoes based on the noise level analyzed (Step S303). While the normal threshold is a relatively large threshold L1 as illustrated in FIG. 10, the threshold determined here is determined as a threshold L2 that is slightly over a noise level LN. As illustrated in FIG. 10, the bottom echo is detected at a point P1 when the normal threshold L1 is the threshold, and is detected at a point P2 slightly over the noise level when the threshold L2 is the threshold. As a consequence, even a faint bottom echo can be detected.

The signal analyzing unit 12 then, as the same as that in the second example, calculates the echo heights of the bottom echoes EB in the designated section from the ultrasonic data stored in the wave memory 11 (Step S304). Furthermore, the signal analyzing unit 12, as the same as that in the second example, calculates the beam path lengths in the designated section at Step S305, and calculates the beam path-length change rates in the designated section at Step S306.

The flaw detector 13 then, as the same as that in the second example, determines whether there is a point present at which the beam path length is equal to or smaller than the threshold DB, or the absolute value of the beam path-length change rate is equal to or greater than the threshold DC2 and the echo height is equal to or smaller than the threshold DA (Step S307). The threshold DC2 here is a value smaller than that of the threshold DC as described above. When the point at which the beam path length is equal to or smaller than the threshold DB, or the absolute value of the beam path-length change rate is equal to or greater than the threshold DC2 and the echo height is equal to or smaller than the threshold DA is present (Yes at Step S307), the flaw detector 13 determines that a flaw is present at the point (location) at which this condition is satisfied (Step S308). Meanwhile, when the point at which the beam path length is equal to or smaller than the threshold DB, or the absolute value of the beam path-length change rate is equal to or greater than the threshold DC2 and the echo height is equal to or smaller than the threshold DA is not present (No at Step S307), the flaw detector 13 determines that no flaw is present in the designated section (Step S309).

The flaw detector 13 then determines whether a subsequent designated section is present (Step S310). If a subsequent designated section is present (Yes at Step S310), the flaw detector 13 moves back to the process at Step S301 to perform the above-described process on the subsequent designated section, and if a subsequent designated section is not present (No at Step S310), the flaw detector 13 ends the present process.

In the third example, the noise level is taken into consideration and the bottom echo is detected by the threshold L2 that is slightly over the noise level, and thus a flaw for which the bottom echo is faint can be detected.

Figure 9:
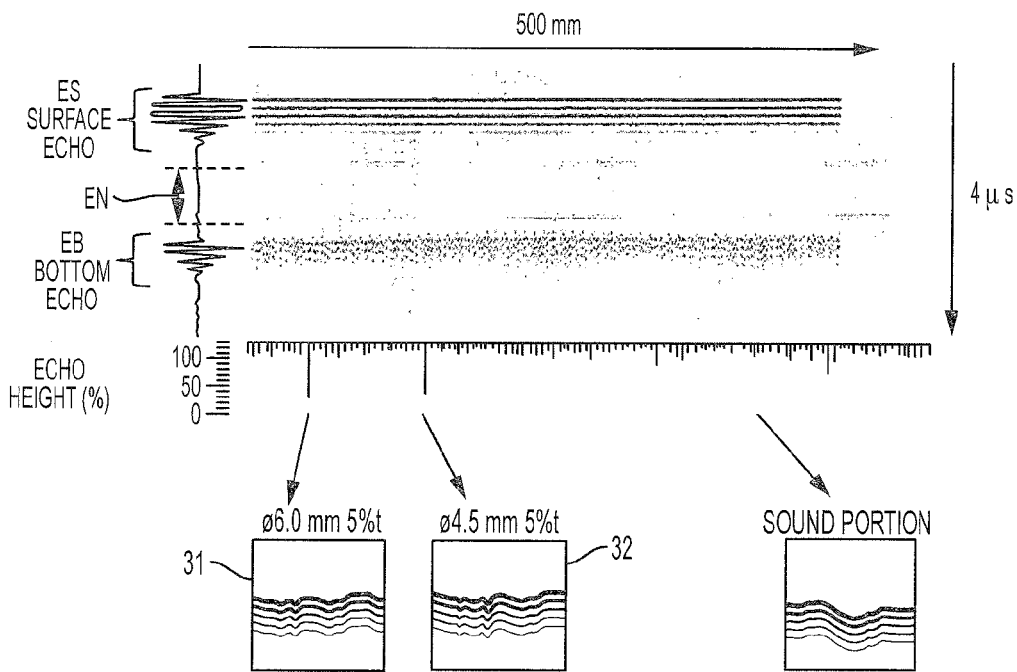
FIG. 9 is a diagram illustrating an example of ultrasonic data to which the third example is applied.
Figure 10:
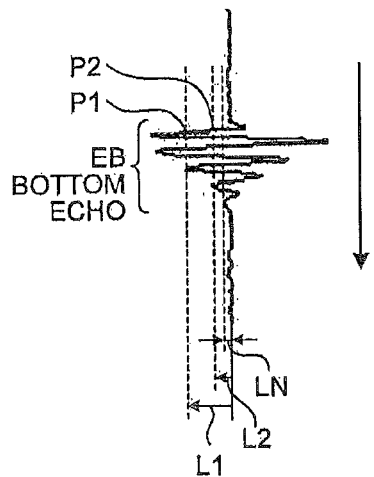
FIG. 10 is a diagram explaining a threshold to detect bottom echo in the third example.
Figure 11:
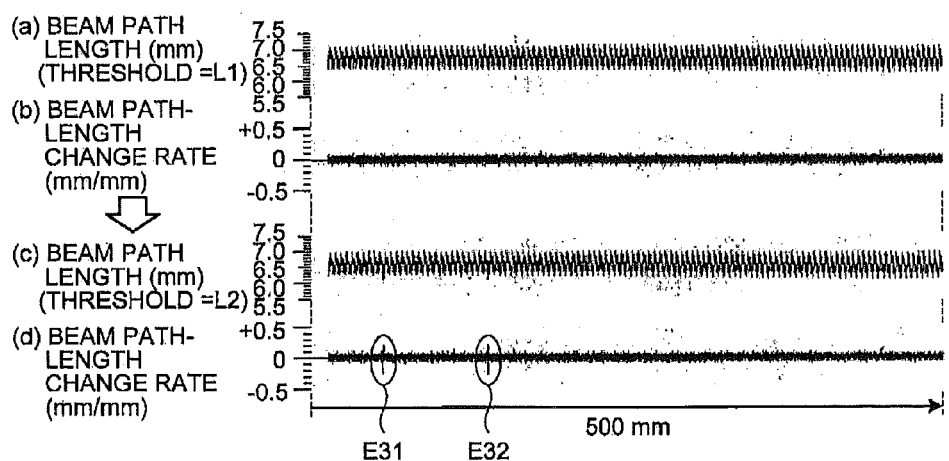
FIG. 11 includes diagrams illustrating the changes in the beam path-length change rate with respect to flaws when the thresholds illustrated in FIG. 10 are changed.

For example, in the ultrasonic data illustrated in FIG. 9, although the bottom echoes of flaws 31 and 32 are small, because the small threshold L2 is used to detect the bottom echoes at such flaws 31 and 32, even the flaws 31 and 32 that are not detectable with the large threshold L1 as the beam path-length change rate illustrated in FIG. 11(*b*), the flaws 31 and 32 are detected in areas E31 and E32 corresponding to the flaws 31 and 32, respectively, as the beam path-length change rate illustrated in FIG. 11(*d*). The flaws 31 and 32 are artificial flaws in a rounded shape having a diameter of 6 millimeters and 4 millimeters, respectively, with a depth of 5 percent formed by electric discharge machining. Furthermore, while there is a portion in which the echo height of the bottom echo is moderately elevated in a sound portion illustrated in FIG. 9, a large change is not found in the portion of the beam path-length change rate corresponding to the sound portion, as illustrated in FIG. 11, and thus it is not determined as a flaw.

Fourth Configuration

Figure 12:
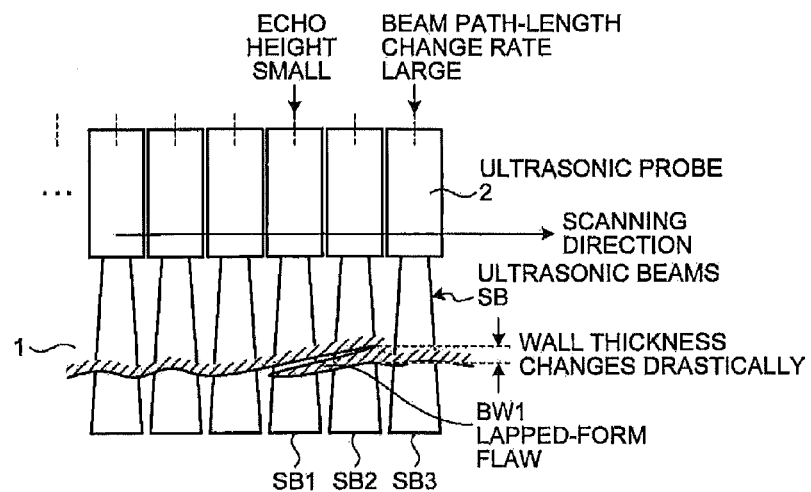
FIG. 12 is a schematic diagram illustrating a condition of ultrasonic flaw detection with respect to a flaw in a lapped form.

In the second and the third examples in the foregoing, the logical conjunction of the beam path-length change rate and the echo height is taken to perform the flaw detection. Depending on the influence of a dent flaw or a flaw in a lapped form arisen on the inner surface of the steel pipe 1, there may be a case in which the flaw is not detectable even when the method in the second or the third example is applied. For example, as illustrated in FIG. 12, when a lapped-form flaw BW1 such as a lapping mark and a galling flaw is present on the inner surface of the steel pipe 1, there have been cases of not being determined as a flaw even when the logical conjunction of the beam path-length change rate and the echo height is taken because the position at which the echo height is equal to or smaller than the threshold DA and the position at which the absolute value of the beam path-length change rate is equal to or greater than the threshold DC or DC2 are slightly shifted from each other. Specifically, in FIG. 12, on the tip side of the lapped-form flaw BW1 that is irradiated with an ultrasonic beam SB1, the surface thereof is inclined, and thus the echo height lowers. Meanwhile, on the base portion side of the lapped-form flaw BW1 that is irradiated with an ultrasonic beam SB3, the wall thickness of the steel pipe 1 changes drastically, and thus the beam path-length change rate increases. More specifically, because the position at which the echo height is equal to or smaller than the threshold DA (position irradiated with the ultrasonic beam SB1) and the position at which the absolute value of the beam path-length change rate is equal to or greater than the threshold DC or DC2 (position irradiated with the ultrasonic beam SB3) are different, there may be a case in which the lapped-form flaw BW1 is not detectable as a flaw as the condition of flaw detection is not satisfied.

Consequently, in a fourth example, when the absolute value of the beam path-length change rate is equal to or greater than the threshold DC or DC2 in the process performed in the second and the third examples, the echo heights within a search range, which is preset with the position of this detection as a reference point, are taken into consideration to perform the flaw detection.

Figure 13:
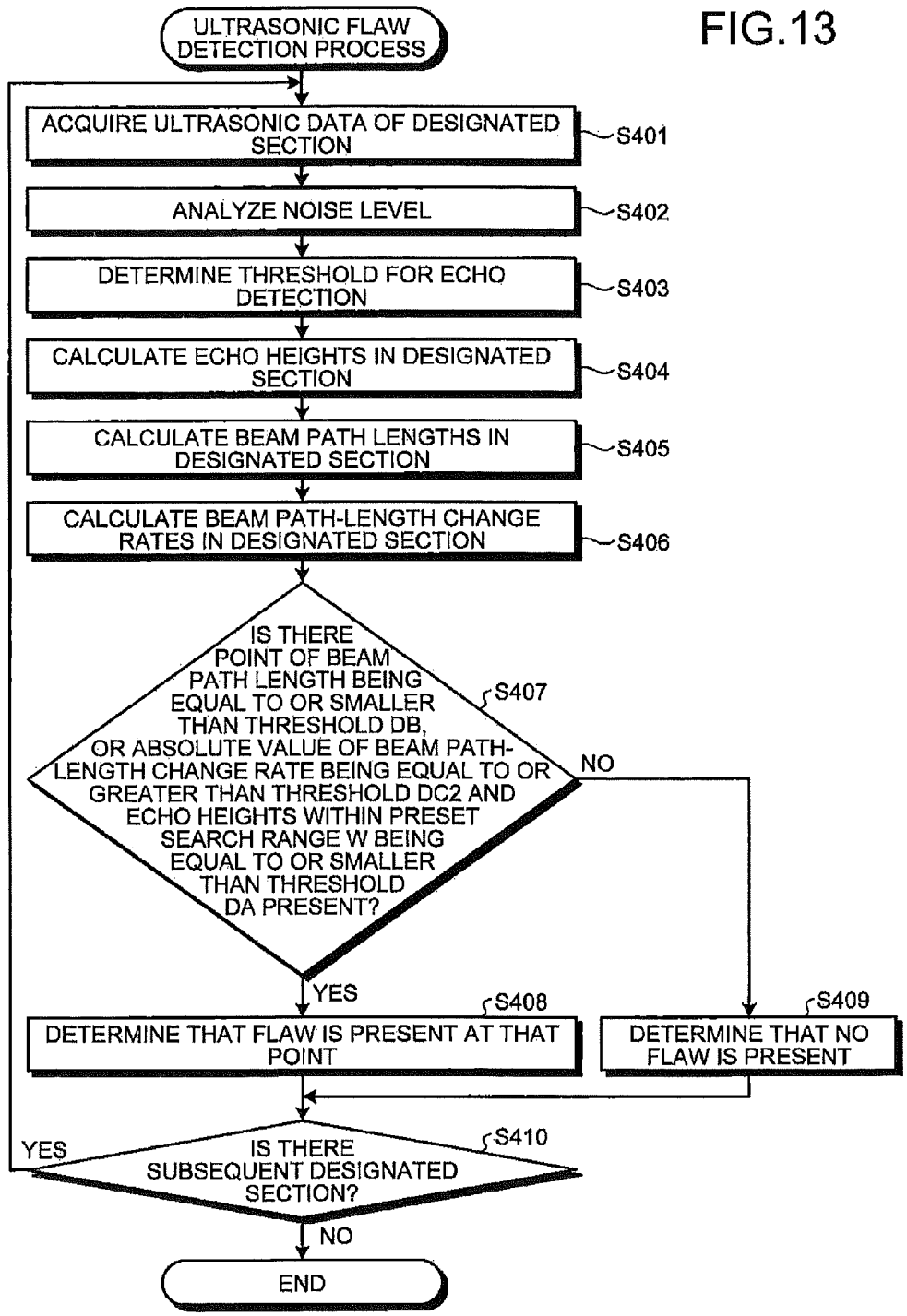
FIG. 13 is a flowchart illustrating a procedure for an ultrasonic flaw detection process performed by a processor according to a fourth example.

With reference to the flowchart illustrated in FIG. 13, the following describes the procedure for an ultrasonic flaw detection process performed by the processor 10 in the fourth example. The controller 15, as the same as that in the second example, first acquires ultrasonic data (B-scope data) of a designated section received from the A/D converter 4, and stores them in the wave memory 11 in sequence (Step S401).

Then, the signal analyzing unit 12, as the same as that in the third example, analyzes noise level from the ultrasonic data stored in the wave memory 11 (Step S402). The signal analyzing unit 12 further determines the threshold to detect bottom echoes based on the noise level analyzed (Step S403). The signal analyzing unit 12 then, as the same as that in the second example, calculates the echo heights of the bottom echoes EB in the designated section from the ultrasonic data stored in the wave memory 11 (Step S404). Furthermore, the signal analyzing unit 12, as the same as that in the second example, calculates the beam path lengths in the designated section at Step S405, and calculates the beam path-length change rates in the designated section at Step S406.

Then, the flaw detector 13, as the same as that in the second example, determines whether there is a point present at which the beam path length is equal to or smaller than the threshold DB, or the absolute value of the beam path-length change rate is equal to or greater than the threshold DC2 and the echo heights within a search range W preset with the position of the absolute value of the beam path-length change rate being equal to or greater than the threshold DC2 as a reference point are equal to or smaller than the threshold DA (Step S407). When the process of analyzing noise level is not performed at Step S402 as the same as that in the second example, the flaw detector 13 determines, at Step S407, whether there is a point present at which the beam path length is equal to or smaller than the threshold DB, or the absolute value of the beam path-length change rate is equal to or greater than the threshold DC and the echo heights within the search range W preset with the position of the absolute value of the beam path-length change rate being equal to or greater than the threshold DC as a reference point are equal to or smaller than the threshold DA.

If the point at which the beam path length is equal to or smaller than the threshold DB, or the absolute value of the beam path-length change rate is equal to or greater than the threshold DC2 and the echo heights within the search range W preset with the position of the absolute value of the beam path-length change rate being equal to or greater than the threshold DC2 as the reference point are equal to or smaller than the threshold DA is present (Yes at Step S407), the flaw detector 13 determines that a flaw is present at the point (location) at which this condition is satisfied (Step S408). Meanwhile, when the point at which the beam path length is equal to or smaller than the threshold DB, or the absolute value of the beam path-length change rate is equal to or greater than the threshold DC2 and the echo heights within the search range W preset with the position of the absolute value of the beam path-length change rate being equal to or greater than the threshold DC2 as the reference point are equal to or smaller than the threshold DA is not present (No at Step S407), the flaw detector 13 determines that no flaw is present in the designated section (Step S409).

The flaw detector 13 then determines whether a subsequent designated section is present (Step S410). If a subsequent designated section is present (Yes at Step S410), the flaw detector 13 moves back to the process at Step S401 to perform the above-described process on the subsequent designated section, and if a subsequent designated section is not present (No at Step S410), the flaw detector 13 ends the present process.

Figure 14:
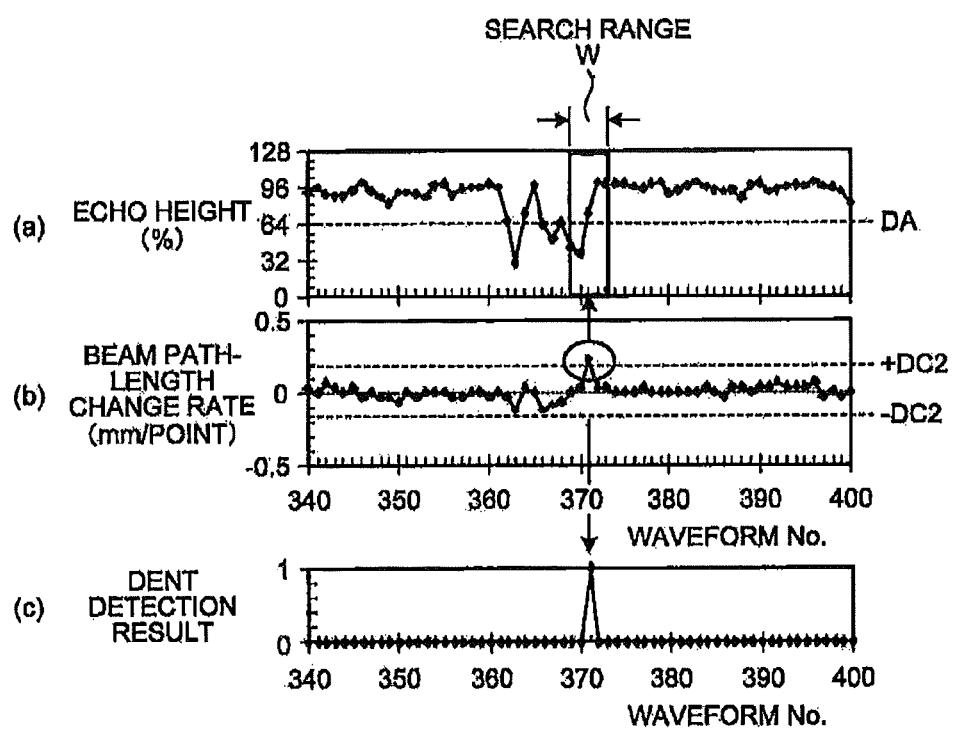
FIG. 14 includes diagrams illustrating a condition of detecting a flaw in a lapped form in the fourth example.

FIG. 14 includes diagrams illustrating an example of flaw detection to which the fourth example was applied. In FIG. 14, the abscissa axis represents waveform numbers in the order of scan. While the beam path-length change rate illustrated in FIG. 14(b) is equal to or greater than the threshold DC2 at the waveform number 371, the echo height at the waveform number 371 illustrated in FIG. 14(a) is not equal to or smaller than the threshold DA, and thus when the second or the third example in the foregoing is applied, it is not detected as a flaw. Furthermore, while the echo height illustrated in FIG. 14(a) is equal to or smaller than the threshold DA at the waveform number 370, the beam path-length change rate illustrated in FIG. 14(b) at the waveform number 370 is not equal to or greater than the threshold DC2, and thus it is not detected as a flaw. In contrast, in the fourth example, with the waveform number 371 for which the beam path-length change rate is equal to or greater than the threshold DC2 as a reference and two points before and after the reference point in scanning direction, more specifically, a total of five points as the search range W preset, the echo height is searched. As a result, the echo heights of the waveform numbers 370 and 369 are equal to or smaller than the threshold DA, and thus a flaw is determined to be present at the waveform number 371.

In the fourth example, a flaw is determined to be present when there is a point present at which the beam path length is equal to or smaller than the threshold DB, or the absolute value of the beam path-length change rate is equal to or greater than the threshold DC2 and the echo heights within the search range W preset with the position of the absolute value of the beam path-length change rate being equal to or greater than the threshold DC or DC2 as a reference point are equal to or smaller than the threshold DA. Thus, a flaw such as a flaw in a lapped form, which may cause the position of the echo height to be equal to or smaller than the threshold DA and the position of the absolute value of the beam path-length change rate to be equal to or greater than the threshold DC or the threshold DC2 to differ slightly, can be detected highly accurately.

First Modification

While the signal analyzing unit 12 calculates the beam path-length change rate by Expression 1 in the first to the fourth examples in the foregoing, it is not limited to this. For example, assuming that the beam path lengths in the designated section are a one-dimensional signal, the one-directional signal is filtered through a low-pass filter to obtain a removal signal in which steep changes are removed, and the result of subtracting the removal signal from the one-dimensional signal (beam path lengths) may be calculated as the beam path-length change rates. Furthermore, a high-pass filter may be used in place of the low-pass filter. In this case, the signal filtered through the high-pass filter itself is calculated as the beam path-length change rates.

Second Modification

Figure 15:
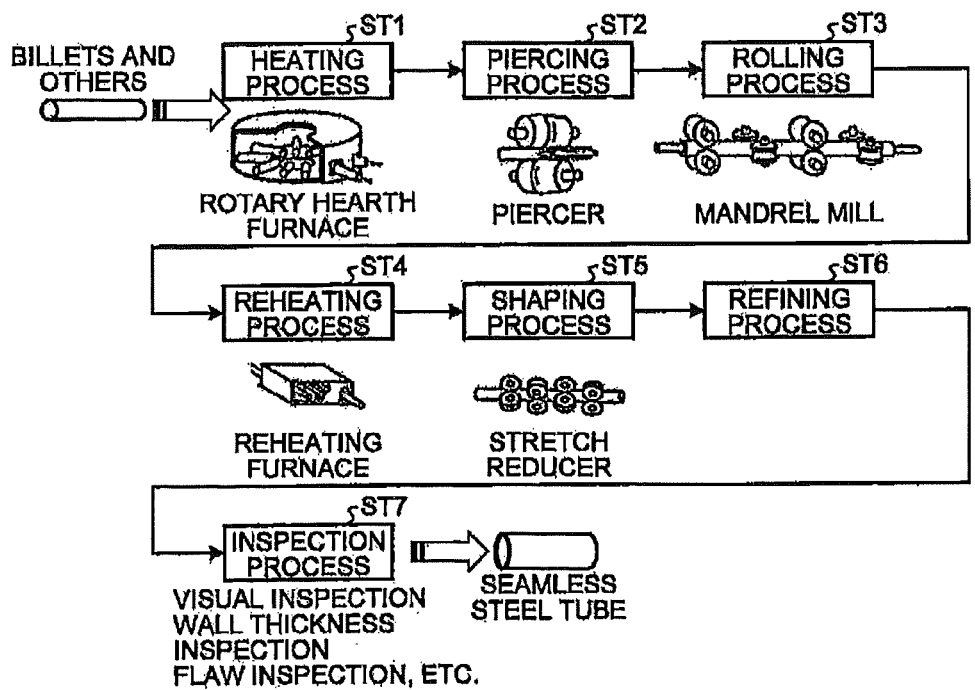
FIG. 15 is a diagram illustrating an example of pipe manufacturing method including an inspection process to which the ultrasonic flaw detection methods in the first to the fourth examples are applied.

In a second modification, the ultrasonic flaw detection methods illustrated in the first to the fourth examples in the foregoing are applied to a method of manufacturing metallic pipes such as the steel pipe 1. For example, the ultrasonic flaw detection methods are applied in an inspection process in the method of manufacturing seamless steel tubes (seamless steel pipes) illustrated in FIG. 15. As for the seamless steel tubes, for example, as illustrated in FIG. 15, round steel slabs such as billets as materials are first heated in a rotary hearth furnace (heating process: ST1), and are then shaped into a hollow tube material by a piercer (piercing process: ST2). The hollow tube material is then rolled by a mandrel mill to reduce the outside diameter and the thickness thereof, and is shaped into an elongated tube material (rolling process: ST3). The elongated tube material is then reheated in a reheating furnace (reheating process: ST4) and is shaped into a finished dimension by a stretch reducer, and after through cooling, straightening, and cutting, the hot rolling is completed (shaping process: ST5). Thereafter, through a refining process (ST6) and an inspection process (ST7), seamless steel tubes that are the final finished products are obtained. In the inspection process, a visual inspection, a wall thickness inspection, a flaw inspection, and others are performed, and in the flaw inspection, the ultrasonic flaw detection methods discussed in the first to the fourth examples in the foregoing are applied.

Third Modification

While the flaw detection process is to be performed after the ultrasonic data for each designated section of, for example, 500 millimeters are acquired in the first to the fourth examples in the foregoing, it is not limited to this. For example, by performing the flaw detection process on a given number of ultrasonic data, for example, the ultrasonic data of each five consecutive points in the scanning direction, a quasi-real-time detection process may be performed. In this case, the flaw detection may be performed each time the ultrasonic data for five points are acquired using the ultrasonic data of the five points, or the flaw detection may be performed each time the ultrasonic data for one point is acquired using the ultrasonic data for five points shifted by one point.

The respective constituent elements in the first to the fourth examples and the first to the third modifications in the foregoing can be combined as appropriate.

While the examples to which our methods and apparatus is applied have been explained above, this disclosure is not restricted by the descriptions and drawings of the examples constituting a part of the disclosure. More specifically, other configurations, examples, and operation methods made by those skilled in the art based on the examples are all included within the scope of this disclosure and the appended claims.

The invention claimed is:

1. An ultrasonic flaw detection method to detect flaws on an inner surface of a metallic pipe using ultrasonic waves comprising:
   a waveform holding step that acquires and holds waveform data of an echo signal when an ultrasonic probe that generates ultrasonic signals toward the inner surface and the metallic pipe are moved relative to each other;
   a signal analyzing step that calculates a path length up to receiving an echo signal from the inner surface and a change rate of the path length based on the waveform data held; and
   a flaw detecting step that detects flaws on the inner surface based on the path length and the change rate of the path length,
   wherein
      the signal analyzing step further calculates a height of the echo signal from the inner surface based on the waveform data held, and
      the flaw detecting step determines that a flaw is present in a portion satisfying a condition in which the path length is equal to or smaller than a given path length threshold, or a portion satisfying a condition in which the change rate of the path length is equal to or greater than a given path-length change rate threshold and the height within a search range preset with respect to a position of the change rate of the path length being equal to or greater than a given path-length change rate threshold as a reference position is equal to or smaller than a given height threshold, and the flaw detecting step determines that no flaw is present in a portion not satisfying the condition.

2. The method according to claim 1, wherein the signal analyzing step analyzes a noise level of noise components in a portion in which no echo signal is present based on the waveform data held, determines a threshold to detect an echo signal based on the analysis result, and detects the echo signal based on the determined threshold to calculate the path length.

3. An ultrasonic flaw detection apparatus that detects flaws on an inner surface of a metallic pipe using ultrasonic waves comprising:
   a waveform holding unit that acquires and holds waveform data of an echo signal when an ultrasonic probe that generates ultrasonic signals toward the inner surface and the metallic pipe are moved relative to each other;
   a signal analyzing unit that calculates a path length up to receiving an echo signal from the inner surface and a change rate of the path length based on the waveform data held; and
   a flaw detecting unit that detects a flaw on the inner surface based on the path length and the change rate of the path length,
   wherein
      the signal analyzing unit further calculates a height of the echo signal from the inner surface based on the waveform data held, and
      the flaw detecting unit determines that a flaw is present in a portion satisfying a condition in which the path length is equal to or smaller than a given path length threshold, or a portion satisfying a condition in which the change rate of the path length is equal to or greater than a given path-length change rate threshold and the height within a search range preset with respect to a position of the change rate of the path length being equal to or greater than a given path-length change rate threshold as a reference position is equal to or smaller than a given height threshold, and the flaw detecting step determines that no flaw is present in a portion not satisfying the condition.

4. The apparatus according to claim 3, wherein the signal analyzing unit analyzes a noise level of noise components in a portion in which no echo signal is present based on the waveform data held, determines a threshold to detect an echo signal based on the analysis result, and detects the echo signal based on the determined threshold to calculate the path length.

5. A pipe manufacturing method in which at least a heating process, a piercing process, a rolling process, a reheating process, a shaping process, and an inspection process are performed on a metallic material to manufacture a pipe, the inspection process comprising:
   a waveform holding step that acquires and holds waveform data of an echo signal when an ultrasonic probe that generates ultrasonic signals toward an inner surface of the pipe and the pipe are moved relative to each other;
   a signal analyzing step that calculates a path length up to receiving an echo signal from the inner surface and a change rate of the path length based on the waveform data held; and
   a flaw detecting step that detects flaws on the inner surface based on the path length and the change rate of the path length,
   wherein
      the signal analyzing step further calculates a height of the echo signal from the inner surface based on the waveform data held, and
      the flaw detecting step determines that a flaw is present in a portion satisfying a condition in which the path length is equal to or smaller than a given path length threshold, or a portion satisfying a condition in which the change rate of the path length is equal to or greater than a given path-length change rate threshold and the height within a search range preset with respect to a position of the change rate of the path length being equal to or greater than a given path-length change rate threshold as a reference position is equal to or smaller than a given height threshold, and the flaw detecting step determines that no flaw is present in a portion not satisfying the condition.

6. The method according to claim 5, wherein the signal analyzing step analyzes a noise level of noise components in a portion in which no echo signal is present based on the waveform data held, determines a threshold to detect an echo signal based on the analysis result, and detects the echo signal based on the determined threshold to calculate the path length.

* * * * *